United States Patent [19]

Umeda et al.

[11] 4,246,073
[45] Jan. 20, 1981

[54] PROCESS OF DISTILLATION OF A MULTICOMPONENT HYDROCARBON MIXTURE

[75] Inventors: Tomio Umeda, Ichikawa; Katsuo Shiroko, Tokyo; Kazuo Niida; Johtaro Itoh, both of Yokohama, all of Japan

[73] Assignee: Chiyoda Chemical Engineering & Construction Co., Ltd., Yokohama, Japan

[21] Appl. No.: 971,428

[22] Filed: Dec. 20, 1978

[30] Foreign Application Priority Data

Dec. 27, 1977 [JP] Japan .................................. 52-156524

[51] Int. Cl.³ .............................................. B01D 3/14
[52] U.S. Cl. ........................................ 203/25; 203/27; 208/353; 208/365
[58] Field of Search ...................... 203/21, 25, 27, 100, 203/23, 22; 62/31, 96, 113; 196/134; 208/353, 365

[56] References Cited

U.S. PATENT DOCUMENTS 2,180,435   11/1939   Schlitt ..................................... 62/31

OTHER PUBLICATIONS

"Energy Requirements of Separation Processes", King, McGraw-Hill (1971).
"A Thermodynamic Approach to Heat Integration in Distillation Systems", Umeda et al., 85th Nat. Aiche Mfg, (1978).

*Primary Examiner*—Frank Sever
*Attorney, Agent, or Firm*—Armstrong, Nikaido, Marmelstein & Kubovcik

[57] ABSTRACT

A process for distilling multicomponent hydrocarbon mixtures in which the relative volatility between the dominant component in the lightest product and the dominant component in the heaviest component is between 1.10 and 7. The hydrocarbon mixture is fed to groups of distillation columns each of which is provided with an overhead condenser and a bottom reboiler, the columns being arranged in succession to receive the product from the prior adjacent column. The operating pressure in the columns increases from the first column to the final column within prescribed limits and the products of the mixture are separately recovered at one time in the final column without being withdrawn from intermediate distillation columns. Heat is recovered from heat source streams of the process by heat exchange with heat sink streams by bringing the streams successively in contact with a plurality of groups of heat exchangers, each group being at a different temperature level.

1 Claim, 8 Drawing Figures

$Q_C$ : HEAT ENERGY OF A HEATING PROCESS
$Q_R$ : HEAT ENERGY OF A HEAT RECOVERY PROCESS
$Q_H$ : HEAT ENERGY OF A COOLING PROCESS

umn B, and then the heat recovered from the condenser of distillation column B is utilized to heat the reboiler of distillation column A. A technique utilizing heat repeatedly in this way is called a multi-effect technique. When applying this technique to a ternary system, distillation processes such as shown in FIGS. 3 and 4 may be considered. In these figures distillation column B is operated under a pressure higher than that of distillation column A.

PROCESS OF DISTILLATION OF A MULTICOMPONENT HYDROCARBON MIXTURE

BACKGROUND OF THE INVENTION

1. Field of the Invention

This invention relates to a process for distilling a multicomponent hydrocarbon mixture to produce a plurality of distillate products and in which all the distillation processes are divised so as to save energy and the heat supplied is efficiently recovered.

2. Background of the Invention

Distillation processes in which a multicomponent hydrocarbon mixture is separated into a plurality of distillate products are usually performed in such a way that a plurality of distillation columns, each of which is provided with a reboiler and a condenser, is installed in a proper sequence and the respective products are successively separated. FIG. 1 illustrates one example of such a distillation process with a ternary component system. Since in this type of distillation process the products are repeatedly heated and cooled, the heat energy required for the process is considerably large.

Thus, the economy of this heat energy is of industrially great significance and heretofore, for the purpose of saving energy in these distillation processes a number of systems have been proposed. The following are well-known:

(1) Petlyuk's distillation system;
(2) a distillation system utilizing the multi-effect principle; and
(3) a countercurrent type heat exchange system.

These systems are effectively utilized to reduce the above-described heat energy supply, but when applied to various multicomponent hydrocarbon mixtures, it is found that they inherently have respective limits depending on the properties of the multicomponent hydrocarbon mixtures. Each of the systems will be explained below. Further descriptions of such systems may be found in texts such as "Separation Processes" by C. J. King, McGraw-Hill (1971).

(1) Petlyuk et al proposed that the heat energy required for the distillation of a multicomponent hydrocarbon mixture can be reduced by changing the combination of distillation columns. For the sake of simplicity, an example of a ternary component system is shown in FIG. 2. In the figure the first column sloppy separates the multicomponent mixture while the second column sharply separates the components according to their specifications. The rate of reduction of the heat energy required for the distillation process by the system, however, has a limit, and moreover, is subject to fluctuations depending on the composition of the feed stock. Furthermore, since both the vapor phase stream and the liquid phase stream are mutually exchanged between the adjacent columns Petlyuk's distillation system is difficult to control. Nevertheless, when combined with many other systems, this system can be utilized as a distillation system which has an improved controllability on the whole.

(2) A distillation system utilizing the multi-effect principle.

In the case where use is made in a certain distillation column A of a heat source whose temperature is sufficiently higher than the bottom temperature of the column A, the heat energy of the heat source is sometimes utilized to heat the reboiler of another distillation column B, and then the heat recovered from the condenser of distillation column B is utilized to heat the reboiler of distillation column A. A technique utilizing heat repeatedly in this way is called a multi-effect technique. When applying this technique to a ternary system, distillation processes such as shown in FIGS. 3 and 4 may be considered. In these figures distillation column B is operated under a pressure higher than that of distillation column A.

FIG. 3 illustrates an example using a binary component system, and FIG. 4 illustrates an example using a ternary component system. In the above described system, the rate of reduction of the heat required for the distillation process is determined by the balance between the condenser load in the high pressure distillation column and the reboiler load in the low pressure distillation column. For this reason, a drastic reduction of the required heat energy cannot be expected without the proper choice of the high pressure distillation column. Also, if there is too large a temperature difference between the reboiler and the condenser this system cannot be applied.

(3) Countercurrent type heat exchange system.

In this system, in order to recover the heat from the heat source streams to be heat-exchanged by the heat sink streams there are installed a plurality of heat exchanger groups, which are formed by grouping a number of heat exchangers. The heat sink streams are successively brought into contact with a plurality of heat exchangers in the heat exchanger groups that are at different temperature levels so as to recover the heat from the heat source streams. In this system of heat recovery the heat source and sink streams are brought in countercurrent contact throughout the whole heat exchange system, so that this heat exchange system is a thermodynamically less irreversible system under the given conditions.

However, this system is effective to some degree in reducing the heat required for the distillation process, but when applied simply to the above-described ordinary distillation process, it is found that heat recovery from a condenser at a low temperature level is very difficult. Hence, a drastic recovery of heat cannot be expected.

The present inventors, who thoroughly investigated the prior-known energy saving techniques, and as a result found that the mere application of these techniques to the ordinary distillation process can show only a limited effect, were able to establish a novel technique of distillation of a multicomponent system by the application of the most suitable combination of the multi-effect principle technique and the countercurrent type heat exchange system and by limiting the multicomponent system to which the process is applied as well as the combination of distillation columns.

SUMMARY OF THE INVENTION

In accordance with the distillation system of this invention use is made of distillation columns each of which is provided with an overhead condenser and a bottom reboiler. The raw material oil fed to the first column is fractionated in the distillation columns during the course of the process, but the respective fractions obtained in each column are immediately sent to the subsequent distillation column without being recovered as intermediate products, and all the products are separated at one time in the final distillation column. The merit of this system is that the heat energy to be supplied to the reboiler of the distillation column can be reduced to the utmost.

A further characteristic of the distillation system according to the present invention is that since the distillation column used in each stage constitutes an independent distillation column provided with an overhead condenser and a bottom reboiler, the operating pressure of each distillation column can be set independent of the others, so that by setting the operating pressure in such a way that the later the distillation column comes in the process, the higher the pressure, the temperature levels of the products distilling from the distillation columns and the overhead vapor can be elevated rendering possible the full utilization of the heat being recovered.

However, in order to operate the distillation columns in such a way that the later the stage of the distillation column, the higher the pressure, the balance between the benefit obtained by elevating the temperature levels of the final products and the overhead vapor that are recovered as heat source streams and the disadvantage arising from the increase in the building cost of the distillation columns and the lowering in the separation performance of the distillation columns owing to the increase in the operating pressure in the columns creates an upper limit of operating pressure. That is to say, in the case where a distillation pressure of 0–6 kg/cm$^2$G is employed in the distillation column in the first stage, the difference in the operating pressure between the first and final columns is desirably 2–10 kg/cm$^2$. If conditions are such that the pressure difference between the first and final columns is lower than 2 kg/cm$^2$, application of the multi-effect principle technique becomes difficult as a result of insufficient elevation of the temperature levels of the heat source streams from the distillation columns in the later stages, while under conditions exceeding 10 kg/cm$^2$G the above described disadvantages arising from increases in the operating pressure become too large to be practical.

On the other hand, if the operating conditions of the distillation columns are limited within the above described range of pressure for the purpose of better heat recovery, it follows that the raw material hydrocarbon mixtures to be subjected to the separation procedure are also limited. More particularly, the multicomponent hydrocarbon mixtures usable in this invention are limited to those in which the relative volatility between the dominant component in the lightest product and the dominant component in the heaviest product is between 1.10–7. If the value of relative volatility exceeds 7, the stream going out from the final column approaches the critical temperature of the bottom stream, whereas if it is less than 1.10, the number of stages required in the final column becomes too large to be fit for an actual apparatus.

The heat sink streams under the conditions of the process of the invention are the raw material, the intermediate products, and the streams to be reboiled, and the heat source streams are the final products and the overhead vapors. To take the overhead vapor as one example, the temperature levels of the heat source streams become progressively higher from the initial to final stages, and the temperature levels of the final products at the respective time of distilling out are also different from one another. For this reason, when a number of heat exchangers for recoverying heat from the heat source streams are divided into several groups of heat exchangers according to their temperature levels, and each group of heat exchangers consists of a plurality of heat exchangers in which the partners of the heat exchange are chosen so that the outlet temperatures of the heat sink streams after heat exchange are almost the same and, moreover, so that the outlet temperatures of the heat source streams after heat exchange are also almost the same, the utilization of heat becomes more and more effective. Thus, the heat sink streams can be fed successively to respective groups of heat exchangers differing in the temperature level until they are heated to a desired temperature level very resonably and without a singificant heat loss, and so that the heat can be best utilized on the whole.

Now, with reference to the drawings this invention will be explained more fully.

BRIEF DESCRIPTION OF THE DRAWINGS

FIG. 5 is a conceptional systematic diagram of a distillation process for carrying out the separation of a three component hydrocarbon mixture for the brief illustration of this invention. FIG. 6 is a systematic diagram showing conceptionally the heat exchange system in the distillation process of FIG. 5 and FIG. 7 is a systematic diagram showing in more detail the group of heat exchangers of FIG. 6.

In FIG. 5 the distillation process for practicing this invention consists essentially of the following three operations:

(1) separation operations by the use of distillation columns, A and B;

(2) heating operations for raw material and intermediate products, C, E, and F; and heating operations by reboilers, D and G; and (3) cooling operations for the products, J, K and L; and cooling operations by condensers, H and I.

The raw material mixture is supplied through supply pipe 1 to distillation column A, being heated with feed preheater C. Distillation Column A is heated by reboiler D, and cooled by condenser H. From distillation column A the intermediate products are distilled out through distillation pipes 2 and 3. These intermediate products are respectively heated by heating operations E and F and then supplied to distillation column B, which is heated by reboiler G and cooled by condenser I. From distillation column B products are distilled out through distillation pipes 4, 5 and 6. The products are cooled to the desired temperatures with product coolers J, K, and L. Distillation column B is operated under a pressure higher than that of distillation column A.

The heat energy required for the distillation process is not equal to the total heat of the heating operations. It is the heat energy obtained by subtracting (1) the heat recovered from one part of the cooling operations at reasonable temperature differences from (2) the total heat of the heating operations. This heat recovery can be achieved most effectively in the process according to the present invention by the system shown in FIG. 6. In this system the streams subjected to the heating operation are the heat sink streams, and the streams subjected to the cooling operation are the heat source streams.

Figure 5:
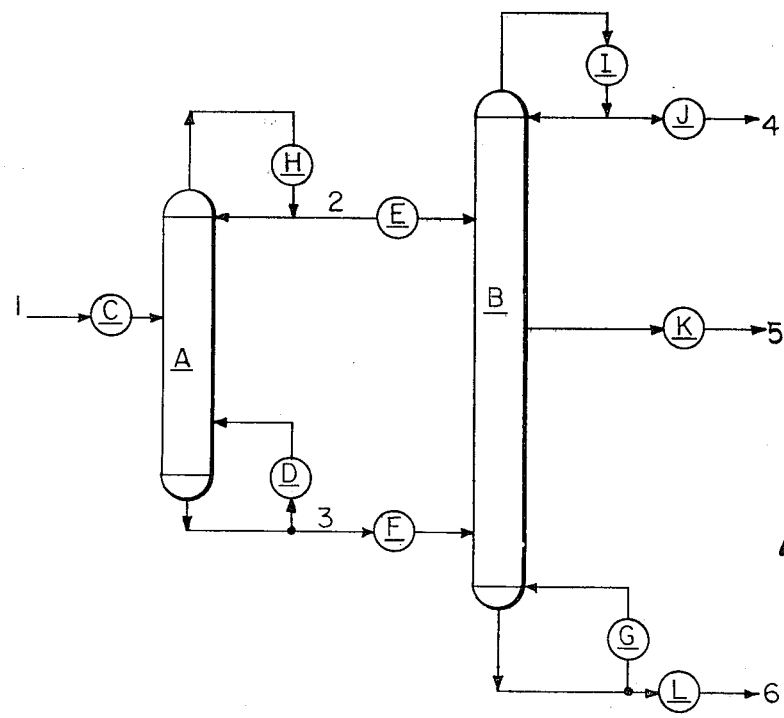
FIG. 5 is an illustration of conceptional systematic diagrams illustrating the distillation process of this invention.
Figure 8:
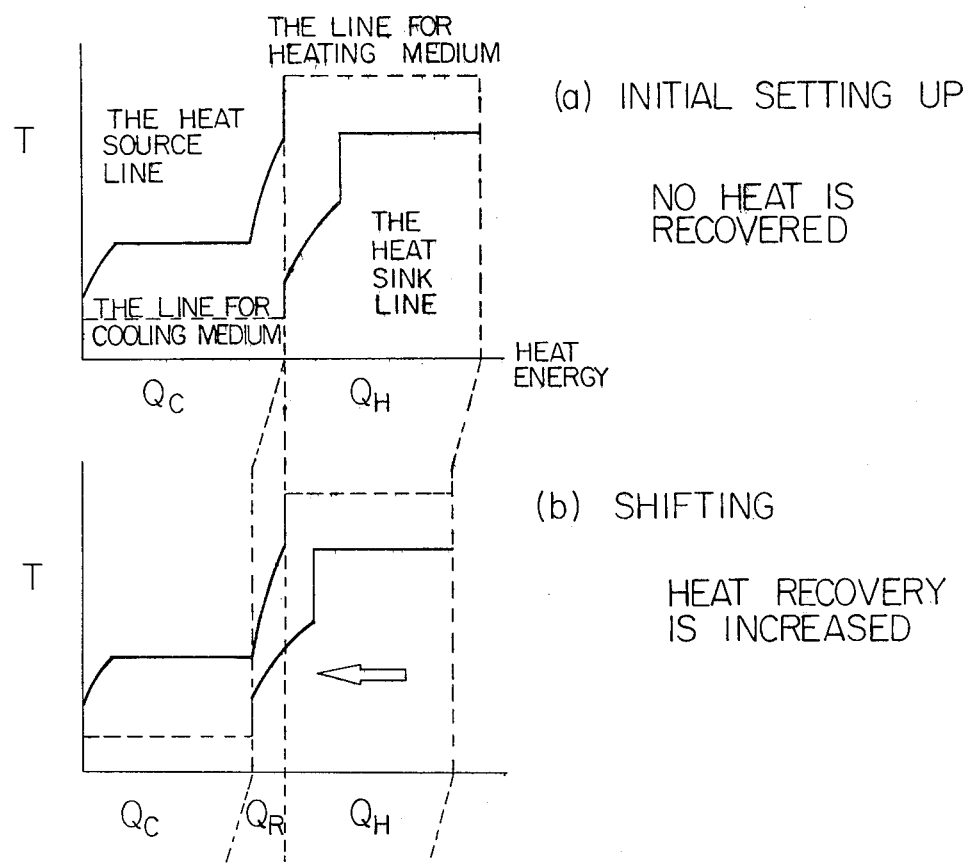
FIG. 8 is a heat availability diagram illustrating a heat source line, a heat sink line, a line for heating medium and a line for cooling medium.

The heat exchange system according to the present invention is determined by thermodynamic analysis utilizing the "available energy concept". This technique which involves the use of heat availability diagrams and so-called T-Q diagrams as shown in FIG. 8 is discussed in a paper by the present inventors entitled "A Thermodynamic Approach to Heat Integration in Distillation Systems" presented at the 85th National AIChE meeting on June 4–8, 1978, in Philadelphia, Pennsylvania. The content of this paper is hereby incorporated by reference and a copy is attached to this application. Thus, for example, utilizing this technique the heat energy in the heating operations as shown in FIG. 5 are summed up at the same temperature levels, and a heat sink line as shown in FIG. 8(a) is prepared by plotting the temperature against the heat energy to be supplied. Similarly, from the heat energy in the cooling operations a heat source line as shown in FIG. 8(a) is prepared by plotting the temperature against the heat energy to be removed.

The heat energy supplied by the heating media and the heat energy removed by the cooling media are respectively adjusted so that the heat energy corresponding to the heat source line can be heat-transmitted to the heat sink streams corresponding to the heat sink line when the heat sink line is set up as shown in FIG. 8(b) under the heat source line leaving a reasonable difference between them by adding the heat energy supplied by the heating media to the high temperature end of the heat source line and adding the heat energy removed by the cooling media to the low temperature end of the heat sink line. The heat transfer is carried out by means of a plurality of heat exchangers.

These heat exchangers are divided into several groups of heat exchangers. The process performed by these groups of heat exchangers is divided into the following three according to the above described heat energy supplied by the heating media and the heat energy removed by the cooling media:

(1) heating process;
(2) heat recovery process; and
(3) cooling process.

The heat exchangers involved in the heating process receive the heat energy from the heating media. The energy saving is promoted by reducing this heat energy.

The heat exchangers involved in the cooling process heat-transfer the heat energy corresponding to the heat source line so as to remove it from there to the cooling media.

The heat exchangers involved in the heat recovery process are the heat exchangers not involved in the heating and cooling process. Thus, the heat exchanger in which the heat energy of the overhead condenser of a certain distillation column is used for the multi-effect as the heat source of the bottom reboiler of another distillation column is a heat exchanger involved in the heat recovery process.

The grouping of the heat exchangers is carried out in such a way that each group of heat exchangers can be a plurality of heat exchangers in which the partners of the heat exchange have been chosen so as to render it possible that the outlet temperatures of the heat sink streams after heat exchange are almost the same, and moreover, the outlet temperatures of the heat source streams after heat exchange are also almost the same. There is generally more than one combination of the heat exchangers in which the outlet temperature of the respective heat sink streams passing through the group of heat exchangers can be almost the same and thus suitable combinations are determined by taking into consideration the number of heat exchangers, the degree of division of each of the streams, and the operability.

Figure 1:
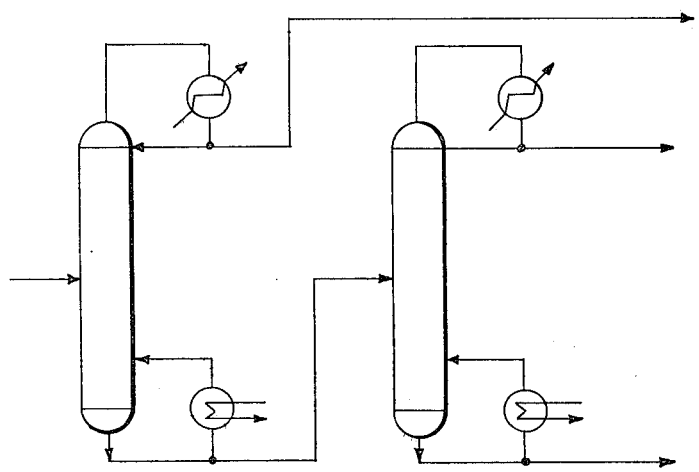
FIG. 1 illustrates a prior known distillation system for a multicomponent hydrocarbon mixture.
Figure 2:
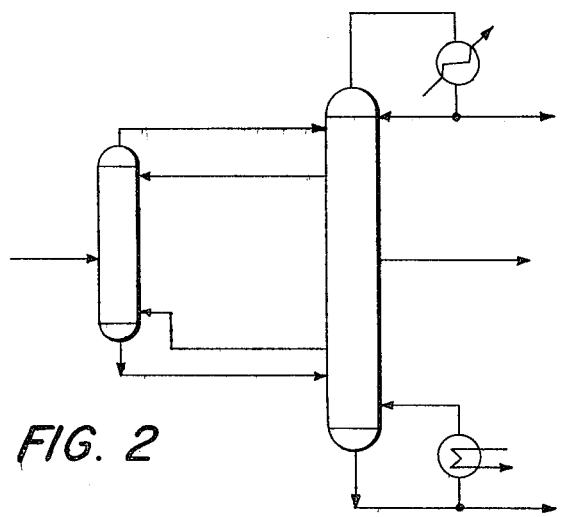
FIG. 2 illustrates Petlyuk's distillation system.
Figure 6:
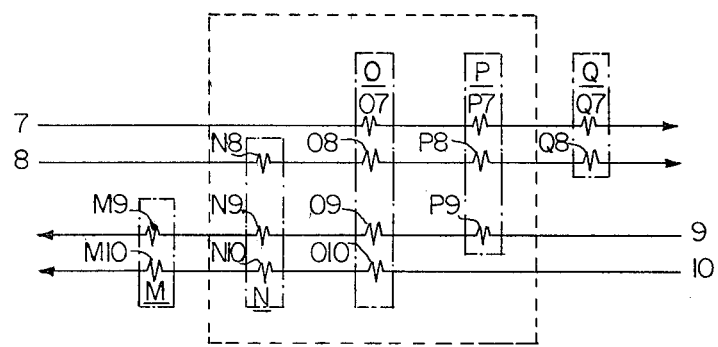
FIG. 6 is a conceptional systematic diagram illustrating the heat exchange system in the distillation process shown in FIG. 5.
Figure 3:
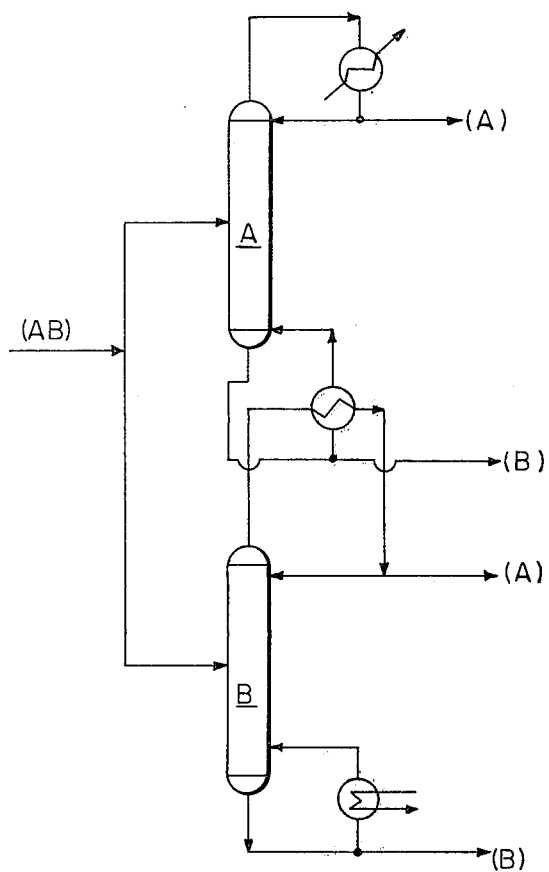
FIGS. 3 and 4 illustrate a distillation system utilizing the multi-effect principle.
Figure 4:
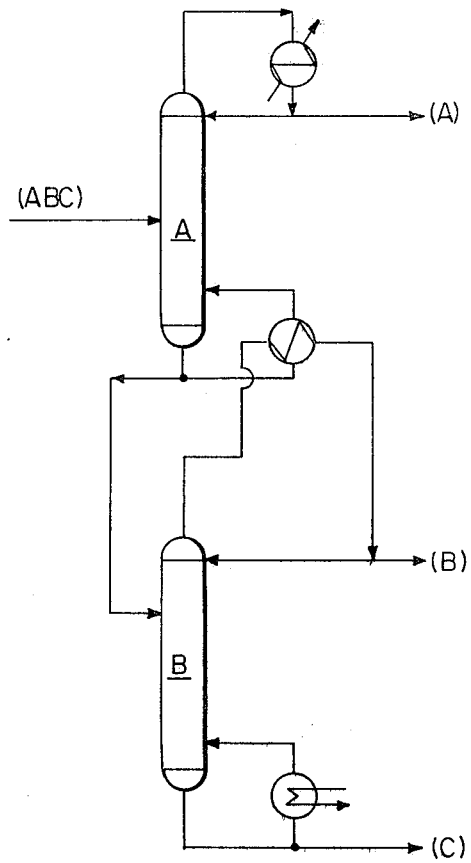

An example of these groups of heat exchangers is shown as a conceptional systematic diagram in FIG. 6, in which for the sake of simplicity in the drawing there have been drawn two transport pipes of the heat source streams (7 and 8) and two transport pipes of the heat sink streams (9 and 10). The portions surrounded by the dotted lines in the figure represent respective groups of heat exchangers, M, N, O, P and Q. The heating process consists of one group of heat exchangers, M; the heat recovery process consists of three groups of heat exchangers, N, O, and P; and the cooling process consists of one group of heat exchangers, Q.

The heat sink streams are heated successively in this way by the use of a plurality of groups of heat exchangers. For instance, the stream 9 in FIG. 6 is firstly brought into contact with a group of heat exchangers P at a low temperature level, and then successively with two groups of heat exchangers O and N at higher temperature levels. In this case each of the groups is devised so as to be able to recover the heat energy by a reasonable temperature difference in almost the same order. Further, it is desirable that the number of groups of heat exchangers is minimized, and moreover, that the heat energy recovered in each group is almost equalized. In this invention, of course, the number of the groups of heat exchangers is limited, and it is usually 2–10, or preferably 2–5, or more preferably 3–4. By considering together the effect of this invention and the disadvantages arising from an increased number of heat exchangers, the number of heat exchangers may be limited as above.

Figure 7:
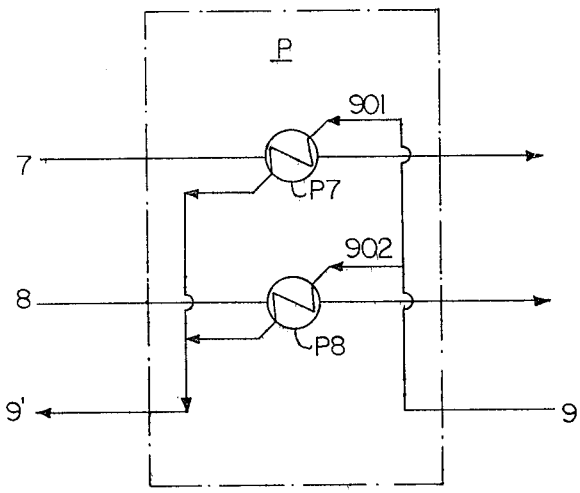
FIG. 7 is a systematic diagram illustrating in more detail the group of heat exchangers shown in FIG. 6.

FIG. 7 illustrates in more detail the group of heat exchangers shown in FIG. 6. For the sake of simplifying the explanation, FIG. 7 indicates only one group of heat exchangers P within the heat recoverying process of FIG. 6. In FIG. 7 heat source streams 7 and 8 and heat sink stream 9 are heat exchanged. Stream 9 is divided into stream 901 and stream 902 without varying the total flow rate. Stream 901 is heated with stream 7, whereas stream 902 is heated with stream 8, and both attain almost the same temperature. These streams 901 and 902 are merged into stream 9'. The system is also devised so as to make the outlet temperature of streams 7 and 8 also almost comparable.

Next, with reference to the example one embodiment of this invention will be explained below.

EXAMPLE

Table 1 sets forth the comparative results obtained when conventional methods and the method of this invention were carried out for the separation of 210,000 t/year of mixture of benzene-toluene-all isomers of xylene. It was assumed that the molar ratio of benzene-toluene-all isomers of xylene was 3:2:1.

As the conventional methods there were chosen the three cases: I, II and III described below.

Case I

According to the ordinary separation method benzene is first separated and then toluene is separated. The operating pressure is 0.3 kg/cm$^2$G in each distillation column.

Case II

Benzene is first separated and then toluene is separated. The operating pressure is 0.3 kg/cm$^2$G in the first column and 4.3 kg/cm$^2$G in the second column.

Case III

According to the distillation process as shown in FIG. 5 benzene, toluene, and all isomers of xylene are respectively distilled from the second column. The operating pressure is 0.3 kg/cm$^2$G in each column.

As the method of this invention there was employed the above described Case III in which the operating pressure in the second column was maintained at 9.3 kg/cm$^2$G. In addition, it should be noted that both in Case II of the conventional method, in which the second column was pressurized, and in the method of this invention, one portion of the heat energy of the overhead condenser of the second column was utilized to heat the bottom reboiler of the first column.

The specifications of the products, benzene, toluene, and all isomers of xylene were respectively more than 97 mole %, 96 mole % and 98 mole %.

TABLE 1

|  | Heat energy supplied to distillation system (10$^6$ Kcal/h) | Reduction of heat energy when taking conventional method (Case I) as the base case (10$^6$ Kcal/h) | Pay out period of supplemental investment when taking conventional method (Case I) as the base case (year) |
|---|---|---|---|
| Conventional method | | | |
| Case I | 5.4 | — | — |
| Case II | 3.5 | 1.9 | 0.5 |
| Case III | 5.2 | 0.2 | 6.8 |
| Method of this invention | 2.9 | 2.5 | 1.1 |

As shown in Table 1 the reduction in heat energy to be supplied is more remarkable in the method of this invention than in any case of the conventional methods. Cases II and III of the conventional methods are obtained by applying the existing energy saving technique to Case I of the conventional methods, while the method of this invention is obtained by the combined use of the multi-effect technique utilized in Case II and the technique of combining distillation columns utilized in Case III. The reduction in the heat energy attained in the method of this invention is larger than the sum of those attained in Case II and III.

Even in the above described embodiment of this invention in which the composition of the hydrocarbon mixture to be separated is far from having a uniform distribution, it is obvious that this invention can contribute to a drastic saving of energy.

Furthermore, when comparing the economics of this invention with that of Case I of the conventional methods as the base case with respect to the pay out period of supplemental investment, the pay out period is found to be only 1.1 years, so that the method of this invention is an extremely economical one.

Although the invention has been described in conjunction with certain embodiments thereof, it is not intended to be limited to these embodiments but instead includes all of those embodiments within the scope and spirit of the appended claims.

What is claimed is:

1. An energy saving process for distilling a multicomponent hydrocarbon mixture in which the multicomponent hydrocarbon mixture is separated into products by means of distillation columns and which comprises:

feeding a hydrocarbon mixture, as a raw material, to a series of at least two distillation columns, said hydrocarbon mixture being a mixture of products in which the relative volatility between the dominant component in the lightest product and the dominaant component in the heaviest product is between 1.10 and 7; said raw material being fed to the first of said series of at least two distillation columns, all of the products of said hydrocarbon mixture being recovered separately and at one time from the last of said series of at least two distillation columns, and all of the products of said first column and columns intermediate said first and last columns being fed separately to the next adjacent column; each of said series of at least two distillation columns having an overhead condenser and a bottom reboiler, the operating pressure in the first column being 0-6 kg/cm$^2$G, the pressure difference between the first and last columns being 2-10 kg/cm$^2$G, and the operating pressure of the distillation columns increasing successively from the first column to the last column; and indirectly contacting (1) as heat source streams, the products of said hydrocarbon mixture recovered from the last column and overhead vapors from each of said at least two distillation columns, and (2) as heat sink streams, the raw material, product streams from the first column and from columns intermediate the first and last columns, and streams to be reboiled, to recover heat energy from the heat source streams by passing the heat sink streams and heat source streams successively through a plurality of groups of heat exchangers, each group of heat exchangers being at a different temperature level, the heat sink streams and heat source streams contacted indirectly in each group of heat exchangers being chosen so that the outlet temperatures of the heat sink streams from each heat exchanger in the group are almost the same and so that the outlet temperatures of the heat source streams from each exchanger in the group are almost the same, and wherein heat is recovered from at least one of the overhead vapors of the distillation columns by said groups of heat exchangers.

* * * * *